United States Patent
Davis (10) Patent No.: US 10,244,994 B2
(45) Date of Patent: Apr. 2, 2019

(54) CT SCAN INFLATABLE MATTRESS

(71) Applicant: David T. Davis, Bethlehem, PA (US)

(72) Inventor: David T. Davis, Bethlehem, PA (US)

(73) Assignee: Woodlark Circle, Inc., Bethlehem, PA (US)

( * ) Notice: Subject to any disclaimer, the term of this patent is extended or adjusted under 35 U.S.C. 154(b) by 188 days.

(21) Appl. No.: 15/231,125

(22) Filed: Aug. 8, 2016

(65) Prior Publication Data

US 2017/0035373 A1 Feb. 9, 2017

Related U.S. Application Data

(60) Provisional application No. 62/202,444, filed on Aug. 7, 2015.

(51) Int. Cl.
| | |
|---|---|
| A61B 6/04 | (2006.01) |
| A61B 6/03 | (2006.01) |
| A61G 1/048 | (2006.01) |
| A61G 7/07 | (2006.01) |
| A61G 7/057 | (2006.01) |
| A61G 7/10 | (2006.01) |

(52) U.S. Cl.
CPC ............ *A61B 6/0485* (2013.01); *A61B 6/032* (2013.01); *A61B 6/0442* (2013.01); *A61G 1/048* (2013.01); *A61G 7/05769* (2013.01); *A61G 7/072* (2013.01); *A61G 7/103* (2013.01); *A61G 2210/50* (2013.01)

(58) Field of Classification Search
CPC ........................................ A61B 6/04
USPC .......................................... 5/601, 600, 636
See application file for complete search history.

(56) References Cited

U.S. PATENT DOCUMENTS

| | | |
|---|---|---|
| 7,266,852 B2 | 9/2007 | Davis |
| 7,406,723 B2 | 8/2008 | Davis |
| 8,387,177 B2 | 3/2013 | Davis |
| 2003/0084512 A1* | 5/2003 | Fujita ................... A61B 6/0421 5/601 |
| 2008/0104762 A1 | 5/2008 | Davis |

* cited by examiner

*Primary Examiner* — Frederick C Conley

(74) *Attorney, Agent, or Firm* — Duane Morris LLP (57) ABSTRACT

An inflatable mattress includes a top panel, a bottom panel, and a side panel coupled between a perimeter of the top panel and a perimeter of the bottom panel. The side panel defines a cutout sized and configured to receive a headrest therein. The top panel defines a fabric section extending over the cutout.

18 Claims, 6 Drawing Sheets

CT SCAN INFLATABLE MATTRESS

CROSS-REFERENCE TO RELATED APPLICATIONS

This application claims priority under 35 U.S.C. § 119(e) to U.S. Provisional Patent Application Ser. No. 62/202,444, filed Aug. 7, 2015, and entitled "CT SCAN INFLATABLE MATTRESS," the entirety of which is incorporated by reference herein in its entirety.

SUMMARY

In various embodiments, an inflatable mattress comprising a headrest cutout is disclosed. In general, the inflatable mattress includes at least a top panel and a bottom panel joined by a side panel. The side panel and the bottom panel define a cutout that is sized and configured to receive a headrest therein.

In various embodiments, an inflatable mattress includes a top panel having a first perimeter and a bottom panel having a second perimeter coupled to the first perimeter. The first perimeter and the second perimeter define a recess sized and configured to receive a headrest therein. A fabric section is coupled to the top panel and extends over the recess.

In various embodiments a method of transporting a patient for medical imaging is disclosed. The method includes positioning a patient over an inflatable mattress. The inflatable mattress including a top panel, a bottom panel, and a side panel coupled between a perimeter of the top panel and a perimeter of the bottom panel. The side panel defines a cutout sized and configured to receive a headrest therein. The inflatable mattress is inflated and positioned on a medical imaging table. A headrest of the imaging table is positioned within the cutout. The inflatable mattress is deflated such that a head of the patient is supported by the headrest of the imaging table. One or more medical images of the patient are acquired.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

The description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise. The term "operatively coupled" is such an attachment, coupling, or connection that allows the pertinent structures to operate as intended by virtue of that relationship. In the claims, means-plus-function clauses, if used, are intended to cover structures described, suggested, or rendered obvious by the written description or drawings for performing the recited function, including not only structure equivalents but also equivalent structures.

Figure 1:
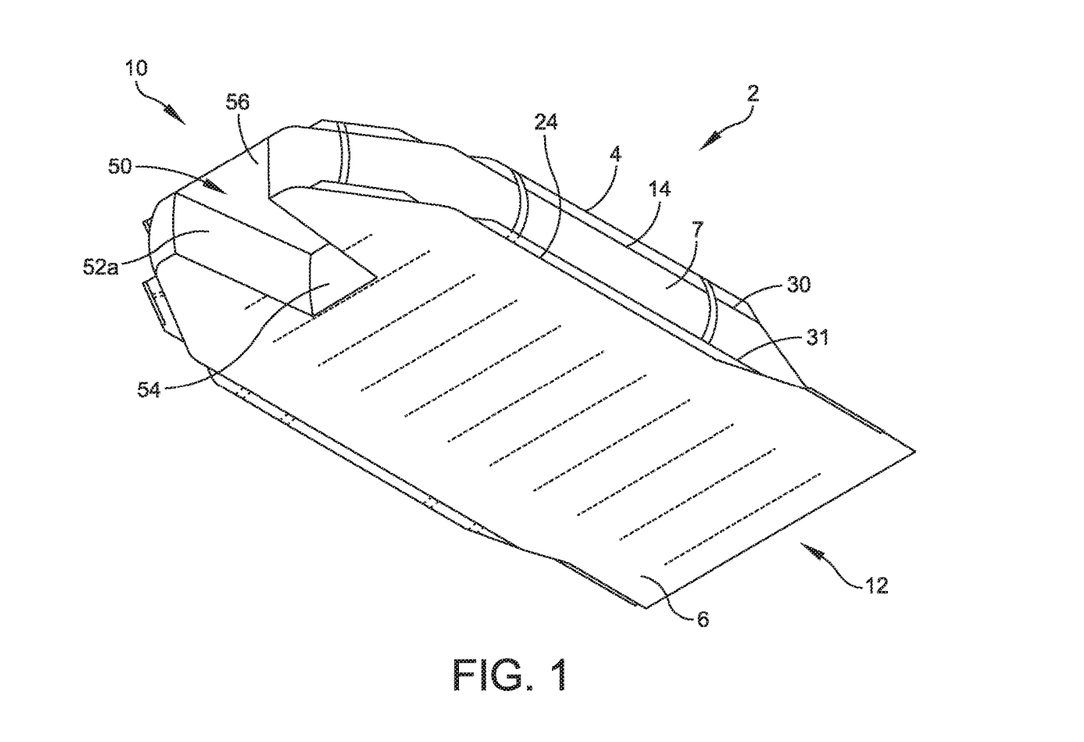
FIG. 1 illustrates a bottom view of an inflatable mattress having a head cut-out defined therein, in accordance with some embodiments.
Figure 2:
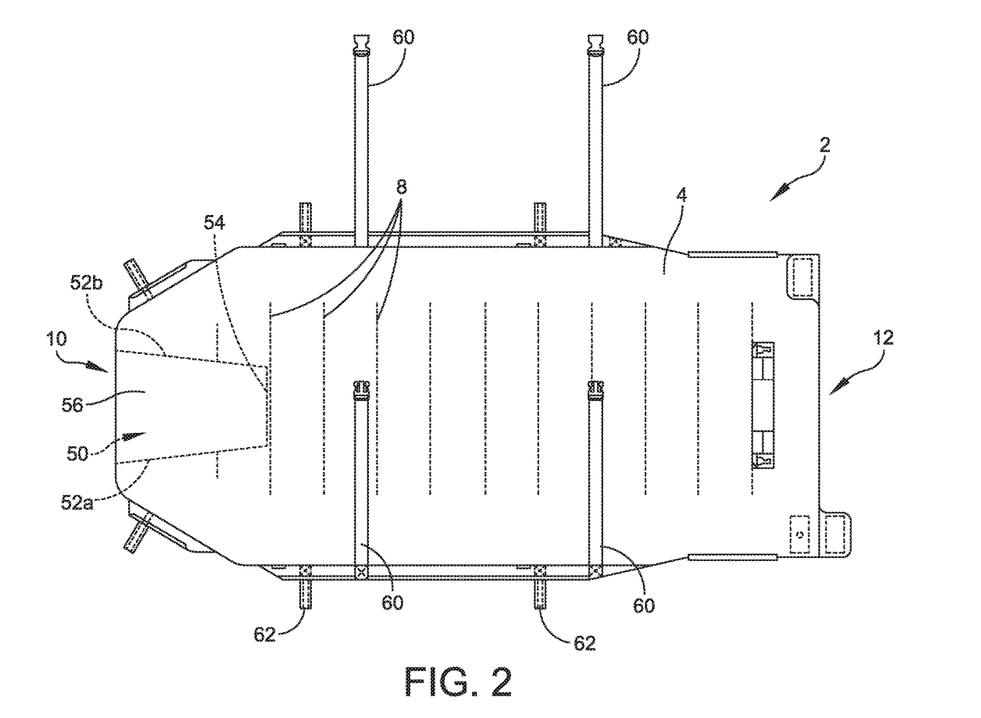
FIG. 2 illustrates a top-down view of the inflatable mattress of FIG. 1.

Referring to FIGS. 1-2, an inflatable mattress 2 is provided including a top panel 4, a bottom panel 6, a perimeter band 7, and a plurality of baffle-panels 8. The top panel 4 includes a head portion 10, a foot portion 12, and a peripheral edge 14. Likewise, the bottom panel 6 includes a head portion, a foot portion, and a peripheral edge, and is substantially similar in peripheral profile to top panel 4. The perimeter band 7 can include an elongate substantially rectangular strip, having a top edge 30 and a bottom edge 31. In some embodiments, top panel 4 and bottom panel 6 are substantially the same size and peripheral outline so that top edge 30 and bottom edge 31 of perimeter band 7 can be sealingly fastened to peripheral edges 14 and 24.

An inlet opening is formed in a portion of perimeter band 7, between peripheral edges 14 and 24, and may be a closeable opening that sealingly accepts an air supply hose. The inlet opening is sized and shaped so that the air supply hose may be inserted, with the inlet being thereafter snapped shut or otherwise closed to hold the air supply hose in place while inflatable mattress 2 is being inflated. The inlet opening may also include a valve (not shown) that is biased to be normally closed to prevent air from exiting the inlet, and opened when the air supply hose is inserted into inlet opening. Other arrangements known to those skilled in the art may be used to inflate inflatable mattress 2. In some embodiments, the perimeter band 7 may be omitted. For example, in some embodiments, the top panel 4 may be directly coupled to the bottom panel 6. In embodiments omitting a perimeter band 7, features identified as being formed on the perimeter band 7, such as, for example, the inlet opening, may be located on the top panel 4, the bottom panel 6, and/or between the top panel 4 and the bottom panel 6. It will be recognized that any embodiment described herein may omit a perimeter band 7 and is within the scope of this disclosure and the claims.

The bottom panel 6 includes a plurality of tiny holes that are defined through its thickness to allow air, that is supplied by a high-pressure air supply to inflatable mattress 2, via the air supply hose, to escape in a controlled manner so as to allow inflatable mattress 2 to be used as a transfer mattress. The air supplied to a transfer-capable embodiment of inflatable mattress 2 escapes through the plurality of holes, providing a weight-bearing cushion of air that facilitates the sliding of inflatable mattress 2 along a surface, as well as, from one surface to another.

The plurality of baffle panels 8 each comprise substantially rectangular sheets of nylon scrim or the like, and include a top edge and a bottom edge (not shown). Baffle-panels 8 may have differing or varying widths, depending upon their position within inflatable mattress 2. Each top edge may be fastened longitudinally or transversely to a portion of the inner surface of top panel 4, and each bottom edge may be fastened longitudinally or transversely to a portion of the inner surface of bottom panel 6. When baffle panels 8 are assembled in a transverse manner, they can have a narrow center section that causes at least top panel 4 to form a longitudinally oriented concave recess which helps to cradle a patient's legs when inflatable mattress 2 is inflated with air. A similar concave recess is formed when baffle panels 8 are assembled in a longitudinal manner.

Some or all of the top panel 4, the bottom panel, 6, the perimeter band 7, and/or the plurality of baffle panels 8 may be formed from a sheet of fabric, e.g., nylon scrim or the like, and may be coated on at least an outer surface with a water proof coating. The water proof coating may be any of the well-known polymeric or elastomeric compounds that are known to be impervious to semi-solids and liquids, such as, blood, urine, feces, hospital strength disinfecting compounds, alcohol, or the like. For example, a nylon twill fabric may be coated on one side with a heat sealable, polyurethane coating (e.g., an inner side) and the outer side coated with a Durable Water Repellent (patient side). A practical benefit associated with the use of the foregoing materials is that inflatable mattress 2 retains a better appearance for longer periods of time during use. A double coated inflatable mattress 2 can be easily wiped down, and can be put back into use more quickly.

Alternatively, in those instances where a single use, single patient mattress is provided, i.e., where patient use lasting less than twenty four hours is desired, some or all of the top panel 4, the bottom panel 6, the perimeter band 7, and/or the plurality of baffle panels 8 may be formed from fibers/fabrics suitable for a single use panel, such as, for example, acetate, acrylic, anidex, aramid, azlon, cotton, elastomer, fluorocarbon, fur, glass, lyocell, melamine, metallic, modacrylic, modal, mosacrylic, novoloid, nylon, nytril, olefin, PAN, PBI, PEEK, Pelco, PEN, PLA, PTT, polyester, polyester-polyarylate, rayon, saran, spandex, sulfar, triacetate, vinal, vinyon, and wool. A common characteristic of the foregoing and like materials is their propensity to stain or discolor as a result of contact with blood, urine, feces, hospital strength disinfecting compounds, alcohol, or the like. Additional, a variety of films may be used to form a single patient, single use transfer mattress 2, for example, copolyester, copolyether, ethylene, vinyl acetate, fluorocarbon, polyamide, olefins, polybutylene, polycarbonate, polyester, polystyrene, polyurethane, polyvinyl, alcohol, polyvinyl chloride, polyvinyl fluoride, and plyvinylidene chloride. A practical benefit associated with the use of the foregoing materials is that transfer mattress 2 retains a stained or discolored appearance for longer periods of time after use thereby alerting hospital staff or other care givers that a particular transfer mattress 2 has completed its useful life, and must be discarded.

In one embodiment, some or all of the top panel 4, bottom panel 6, perimeter band 7, and plurality of baffle panels 8 may comprise a cold water soluble partially hydrolyzed polyvinyl alcohol, cold water insoluble hot water disintegrable aliphatic polyester, and minor proportions of processing and performance aids. The aliphatic polyester has a melt temperature above the normal body temperature of a human (37 Degree C.; 98.6 degrees F.) and is present in the resin blend at a concentration sufficient to constitute the continuous phase of the blend. The aliphatic polyester renders the resin blend, and the partially hydrolyzed polyvinyl alcohol in the blend is cold water insoluble and determines the temperature at which articles formed from the blend will be subject to dissolution in an aqueous bath and subsequent disposal. A practical benefit associated with the use of the foregoing material is that transfer mattress 2 not only retains a stained and discolored appearance for longer periods of time after use, thereby alerting hospital staff or other care givers that a particular transfer mattress 2 has completed its useful life, and must be discarded, but also if an attempt is made to launder the mattress after a single use it disintegrates during the washing process. Additional embodiments of inflatable mattresses are disclosed in U.S. Pat. No. 7,266,852, issued Sep. 11, 2007, entitled "Inflatable Transfer Mattress," U.S. Pat. No. 7,406,723, issued Aug. 5, 2008, entitled "Inflatable Mattress and Method for Positioning a Patient," and U.S. Pat. No. 8,387,177, issued Mar. 5, 2013, entitled "Partially Deflatable Transfer Mattress and Method for Transporting a Patient in Comfort," and U.S. Patent App. Pub. No. 2008/0104762, published May 8, 2008, entitled "Transfer Mattress with Device Portal," each of which is incorporated herein by reference it their entireties.

In some embodiments, the head portion 10 of the inflatable mattress 2 defines a headrest cutout 50. The headrest cutout 50 is sized and configured to receive a headrest, such as, for example, a headrest of an imaging machine, therein. In some embodiments, the headrest cutout 50 is defined by the bottom panel 6 and the perimeter band 7. The perimeter band 7 includes a cutout portion defined by sidewalls 52a, 52b and rear wall 54. The bottom panel 6 includes a cutout sized and configured to match the perimeter band 7. The top panel 4 extends over the headrest cutout 50 such that the headrest cutout 50 is covered by a taught fabric section 56 when inflated which supports the patient's head.

A plurality of straps 60 may be coupled to the inflatable mattress 2. In some embodiments, the straps 60 are configured to secure a patient to the inflatable mattress 2. In some embodiments, the straps 60 may configured to couple the inflatable mattress 2 to one or more surfaces, such as, for example, a bedframe. The straps 60 may extend from, for example, the perimeter band 7 of the inflatable mattress, the top edge 30 of the perimeter band 7, and/or the bottom edge 31 of the perimeter band 7. The straps 60 may comprise one or more fasteners, such as, for example, hook-and-loop (e.g., Velcro), snaps, buttons, buckles, and/or any other suitable fixation device. In some embodiments, a plurality of handles 62 are coupled to the inflatable mattress 2. The plurality of handles 62 provide a gripping surface for moving and/or lifting the inflatable mattress 2 when inflated.

Figure 3:
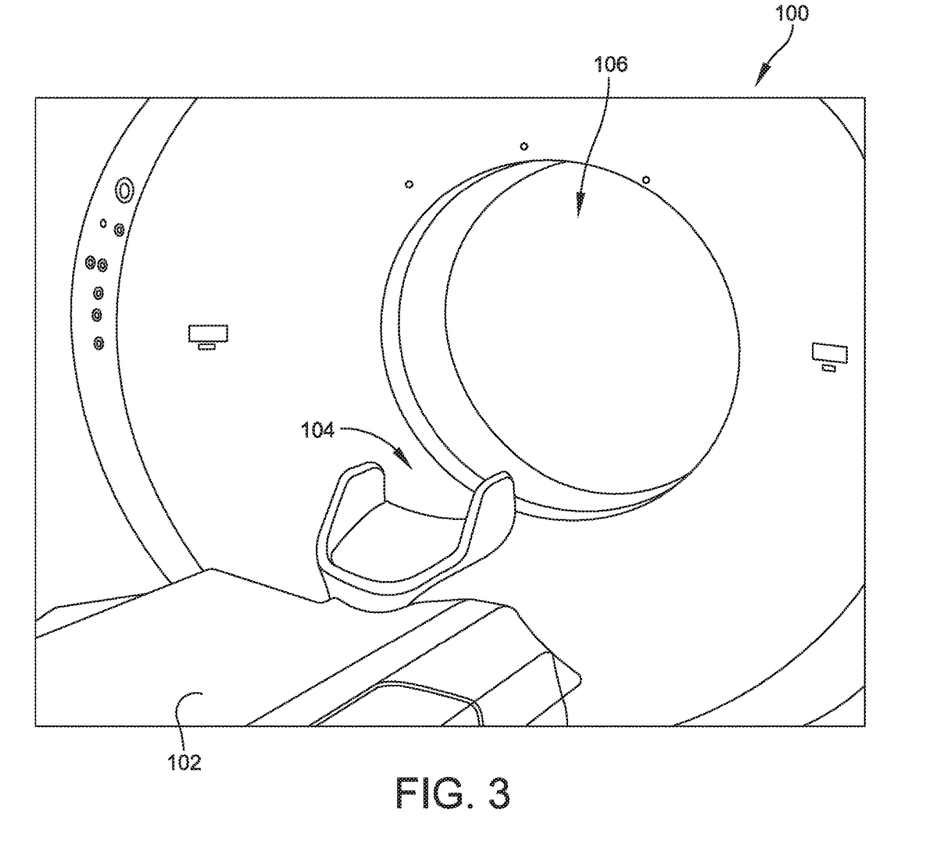
FIG. 3 illustrates a medical imaging device including a patient imaging table having a headrest, in accordance with some embodiments.

The inflatable mattress 2 is configured to facilitate transfer of a patient into a medical imaging machine, such as a CT scanner, without the need to lift the patient. In operation, the inflatable mattress 2 is inflated to transfer the patient from a first surface, such as a hospital bed or gurney. During inflation, the fabric section 56 disposed over the headrest cutout 50 is pulled taught to support the patient's head. Once the inflatable mattress 2 is inflated, the patient may be slid and/or carried from the first surface to a second surface comprising an imaging table or an imaging machine. In some embodiments, a plurality of holes on the bottom surface 6 of the inflatable mattress 2 allow air to escape from the inflatable mattress 2 to facilitate sliding of the inflatable mattress 2. The inflatable mattress 2 is positioned on the imaging table 102 and the headrest cutout 50 is positioned over a headrest 104 of the imaging table 102. The inflatable mattress is deflated in a subsequent step, to lower the patient onto the imaging table 102. Deflation of the inflatable mattress 2 further allows the patient's head to be positioned in the headrest 104 such that the patient's head is maintained in a suitable position during imaging without the need to remove the patient from the inflatable transfer mattress.

Providing easy transportation onto an imaging table while maintaining the patient on the inflatable transfer mattress 2 reduces stresses and potential for injury to both the patient and caregivers during imaging and transfer. Use of the inflatable transfer mattress 2 also facilitates imaging of patients with potential spinal injuries, as the neck and spine can remain immobilized on the inflatable transfer mattress 2 during transfer and imaging without needing to transfer the patient on/off a back-board or other transportation device.

After the imaging has been performed, the inflatable mattress 2 may be re-inflated to lift the patient and the patient's head from the imaging table 102. As the inflatable mattress 2 re-inflates, the height of the inflatable mattress 2 increases to match the height of the headrest 104. The fabric section 58 is pulled taught during inflation, causing the patient's head to lift from the headrest 104 and be supported by the inflatable mattress 2.

Figure 4:
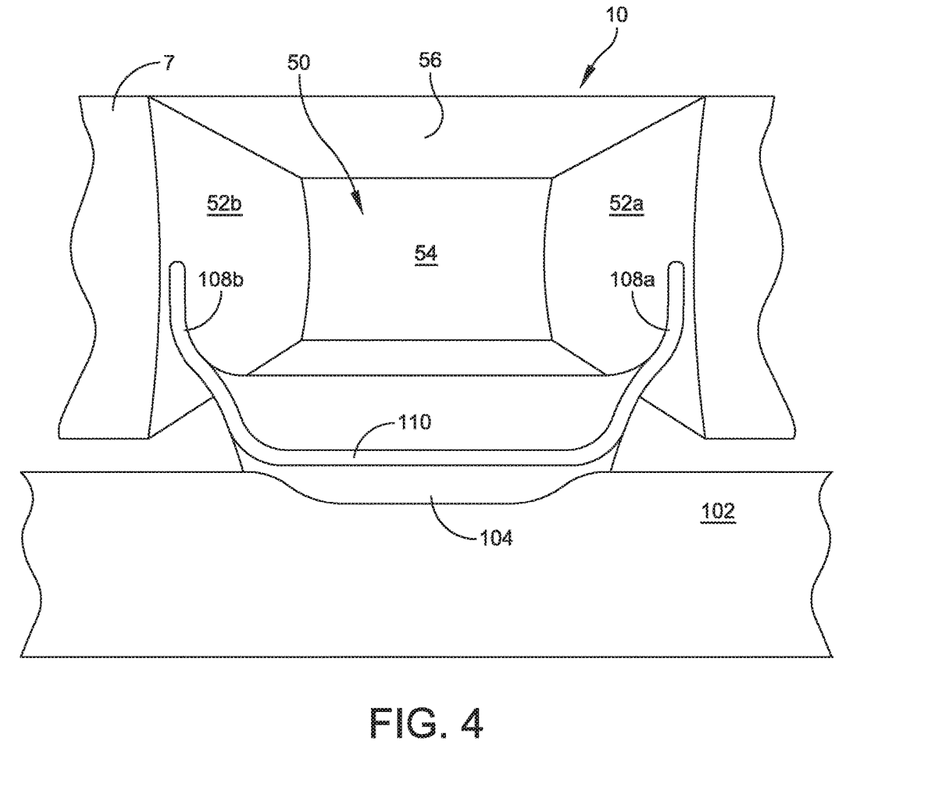
FIG. 4 illustrates the inflatable mattress of FIG. 1 positioned over a medical imaging table in an inflated state, in accordance with some embodiments.

FIG. 4 illustrates one embodiment of an inflatable mattress 2 in an inflated state having a headrest cutout 50 located over the headrest 104 of a CT scan imaging table. As shown in FIG. 4, the headrest cutout 50 is sized and configured to receive the headrest 104 therein. In some embodiments, the headrest cutout 50 has a first width at an open side and a second width at a closed side. The second width can be less than the first width. In some embodiments, the inner walls 52a, 52b of the headrest cutout 50 are tapered to center the inflatable mattress 2 about the headrest 104. In some embodiments, the walls 52a, 52b of the headrest cutout 50 may be straight. The headrest cutout 50 may comprise any width greater than or equal to a width of the headrest 104.

When the inflatable mattress 2 is inflated, the height of the inflatable mattress is greater than or equal to the of the height headrest 104. The inflatable mattress 2 slides over the imaging table 102 to position the patient's head, located on the fabric section 58 of the inflatable mattress 2, above the headrest 104. After the inflatable mattress 2 has been properly positioned, the inflatable mattress 2 can be deflated to lower the patient into position for medical imaging or diagnostic scans.

Figure 5:
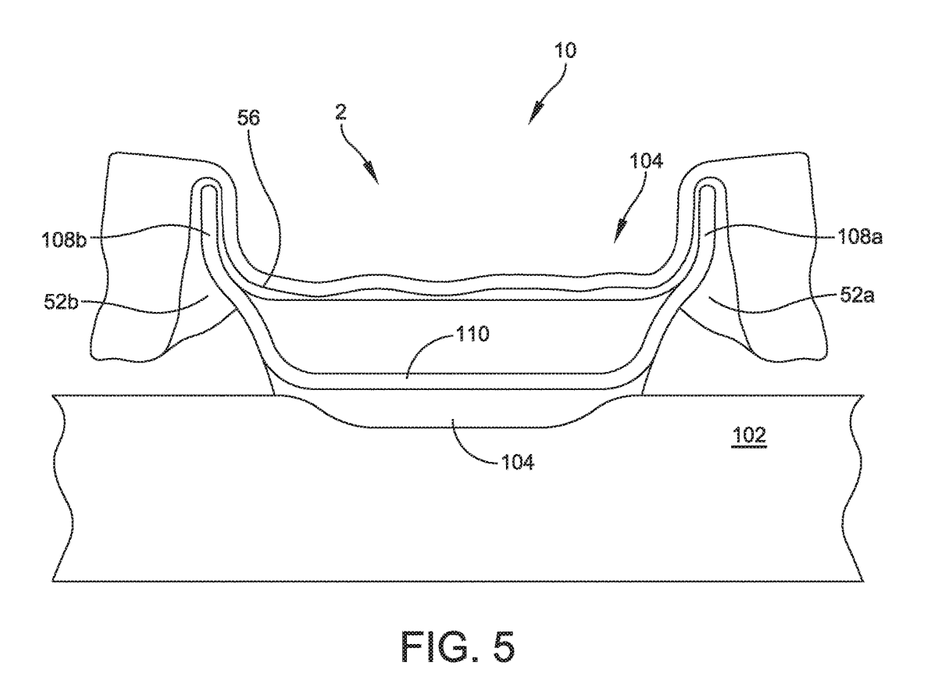
FIG. 5 illustrates one embodiment of the inflatable mattress of FIG. 1 positioned over the medical imaging table in a deflated state.

FIG. 5 illustrates the inflatable mattress 2 of FIG. 4 in a deflated state. The inflatable mattress 2 can be deflated, for example, by one or more deflation valves and/or by the air escaping from the plurality of perforations on the bottom panel 6 of the inflatable mattress 2. When the inflatable mattress 2 is deflated, the weight of the patient's head pulls the fabric section 58 down into the headrest 104. When the inflatable mattress 2 is fully deflated, the fabric section 58 rests directly on top of the headrest 104, which fully supports the weight of the patient's head. Imaging of the patient, such as, for example, CT, MRI, and/or other medical imaging may be performed. After imaging has been completed, the inflatable mattress 2 can be re-inflated to lift the patient from the headrest 104. After the inflatable mattress 2 is fully inflated, the inflatable mattress 2 and the patient can be slideably removed from the CT scan imaging table 102.

Figure 6:
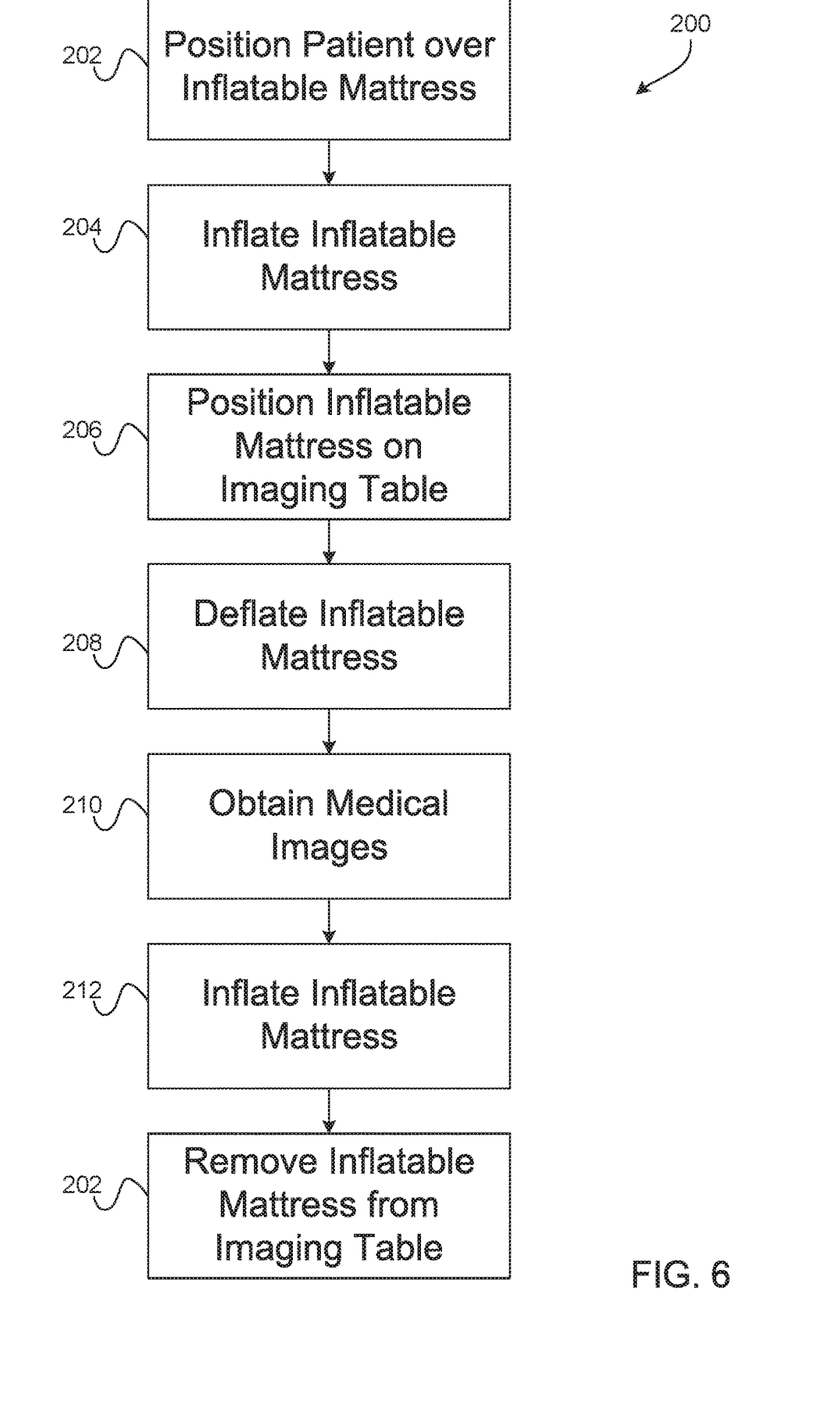
FIG. 6 is a flowchart illustrating a method of positioning a patient using the inflatable mattress of FIG. 1, in accordance with some embodiments.

FIG. 6 illustrates a method 200 of positioning a patient for medical imaging, according to some embodiments. At step 202, a patient is positioned over an inflatable mattress 2. The inflatable mattress 2 includes a cutout 50 defined by one or more of a top panel 4, a bottom panel 6, and/or a side panel 8. In some embodiments, a fabric section 58 extends over the cutout 50 and is configured to support a patient's head. At step 204, the inflatable mattress is inflated using an air source (not shown) coupled to an inlet opening formed in the inflatable mattress 2. The inlet opening can be formed in one or more of the top panel 4, the bottom panel 6, and/or the side panel 8.

At step 206, the inflatable mattress 2 is positioned on a medical imaging table 102. The inflatable mattress 2 can be positioned by sliding and/or lifting of the inflatable mattress 2 and the patient. For example, in some embodiments, the bottom panel 6 defines a plurality of openings extending therethrough. The plurality of openings extend from an inner surface of the bottom panel 6 to an outer surface and allow air to pass from an inner cavity (which receives air via the inlet opening) to the outer surface of the bottom panel. Air escapes through the plurality of holes, providing a weight-bearing cushion of air that facilitates the sliding of inflatable mattress 2 along a surface, as well as, from one surface to another. The inflatable mattress 2 can be slid into position on the imaging table 102. When the inflatable mattress 2 is positioned on the imaging table 102, a headrest 104 of the imaging table 102 is received within the cutout 50 of the inflatable mattress 2.

At step 208, the inflatable mattress is deflated. Deflation of the inflatable mattress 2 can occur through the inlet opening, the plurality of openings in the bottom panel 6, and/or one or more additional deflation openings. Deflation of the inflatable mattress 2 causes the patient to lower onto the medical imaging table 102 and the patient's head to be received within and supported by the headrest 104. At step 210, one or more medical images are obtained.

At step 212, the inflatable mattress 2 is re-inflated to raise the patient off of the medical imaging table 102. Re-inflation of the inflatable mattress 2 causes the fabric section 58 extending over the cutout 50 to become taught and raise the patient's head from the headrest 104. When the inflatable mattress 2 is fully inflated, the patient is entirely supported by the inflatable mattress 2 and the fabric section 58. At step 214, the inflatable mattress is moved from the imaging table, for example, to a gurney or other table for transportation.

Although the subject matter has been described in terms of exemplary embodiments, it is not limited thereto. Rather, the appended claims should be construed broadly, to include other variants and embodiments, which may be made by those skilled in the art.

What is claimed is:

1. An inflatable mattress, comprising:
   a top panel;
   a bottom panel; and
   a side panel coupled between a perimeter of the top panel and a perimeter of the bottom panel, the side panel defining a cutout sized and configured to receive a headrest therein, wherein the side panel comprises an inlet opening sized and configured to couple to an air supply hose.

2. The inflatable mattress of claim 1, wherein the side panel defines a first sidewall and a second sidewall extending from the perimeter of the top panel to a rear wall defined by the side panel, and wherein the first sidewall, the second sidewall, and the rear wall define the cutout.

3. The inflatable mattress of claim 2, wherein the perimeter of the bottom panel defines an opening sized and configured to match the cutout.

4. The inflatable mattress of claim 2, wherein the top panel includes a fabric section extending over the cutout.

5. The inflatable mattress of claim 2, wherein the first and second sidewalls extend from the perimeter of the top panel to the rear wall at an angle such that the cutout defines a first width at a proximal end and a second width at a distal end.

6. The inflatable mattress of claim 5, wherein the first width is greater than the second width.

7. The inflatable mattress of claim 1, comprising a plurality of handles coupled to one or more of the top panel, the bottom panel, or the side panel.

8. The inflatable mattress of claim 1, wherein one or more of the top panel, the bottom panel, or the side panel comprise a single-use panel.

9. An inflatable mattress, comprising:
a top panel;
a bottom panel; and
a side panel coupled between a perimeter of the top panel and a perimeter of the bottom panel, the side panel defining a cutout sized and configured to receive a headrest therein, wherein the bottom panel defines a plurality of perforations defined through a thickness of the bottom panel.

10. An inflatable mattress, comprising:
a top panel having a first perimeter;
a bottom panel having a second perimeter coupled to the first perimeter, wherein the first perimeter and the second perimeter define a recess sized and configured to receive a headrest therein;
a fabric section coupled to the top panel and extending over the recess; and
an inlet opening coupled to one of the top panel or the bottom panel, wherein the inlet opening is sized and configured to couple to an air supply hose.

11. The inflatable mattress of claim 10, comprising a plurality of handles coupled to one or more of the top panel, the bottom panel, or the side panel.

12. The inflatable mattress of claim 10, wherein the recess is tapered such that the recess defines a first width at a open end and a second width at a closed end.

13. A method of transporting a patient for medical imaging, comprising:
positioning a patient over an inflatable mattress, the inflatable mattress including a top panel, a bottom panel, and a side panel coupled between a perimeter of the top panel and a perimeter of the bottom panel, wherein the side panel defines a cutout sized and configured to receive a headrest therein;
inflating the inflatable mattress;
positioning the inflatable mattress on a medical imaging table, wherein a headrest of the imaging table is positioned within the cutout;
deflating the inflatable mattress, wherein a head of the patient is supported by the headrest of the imaging table when the inflatable mattress is deflated; and
acquiring one or more medical images of the patient.

14. An inflatable mattress, comprising:
a top panel having a first perimeter;
a bottom panel having a second perimeter coupled to the first perimeter, wherein the first perimeter and the second perimeter define a recess sized and configured to receive a headrest therein, wherein the bottom panel defines a plurality of perforations defined through a thickness of the bottom panel; and
a fabric section coupled to the top panel and extending over the recess.

15. The method of claim 13, comprising, prior to deflating the inflatable mattress, coupling the inflatable mattress to the medical imaging table using one or more straps coupled to the inflatable mattress.

16. The method of claim 13, wherein the bottom panel of the inflatable mattress includes a plurality of holes defined therethrough, and wherein positioning the inflatable mattress on the medical imaging table comprises sliding the inflatable mattress on the medical imaging table.

17. The method of claim 13, comprising re-inflating the inflatable mattress, wherein the head of the patient is not supported by the inflatable mattress when re-inflated.

18. The method of claim 13, wherein the top panel of the inflatable mattress includes a fabric section extending over the cutout, and wherein the fabric section is received within the headrest of the imaging table.

\* \* \* \* \*